United States Patent [19]

Volkmann

[11] Patent Number: 5,191,077
[45] Date of Patent: Mar. 2, 1993

[54] DIASTEREOMERIC 5R,6S-6-(1R-HYDROXYETHYL)-2-(CIS-1-OXO-3-THIOLANYLTHIO)-2-PENEM-3-CARBOXYLIC ACIDS

[75] Inventor: Robert A. Volkmann, Ledyard, Conn.

[73] Assignee: Pfizer Inc., New York, N.Y.

[21] Appl. No.: 647,400

[22] Filed: Jan. 28, 1991

Related U.S. Application Data

[62] Division of Ser. No. 460,118, Oct. 18, 1989, Pat. No. 5,013,729.

[51] Int. Cl.$^5$ .............. C07D 205/09; C07D 333/48; C07D 301/26; C07D 333/32
[52] U.S. Cl. ........................................ 540/357
[58] Field of Search .......................... 540/357

[56] References Cited

U.S. PATENT DOCUMENTS 4,619,924 10/1986 Hamanaka ..................... 514/195
4,695,626 9/1987 Brightly ........................ 540/310
4,751,297 6/1988 Cue, Jr. ......................... 540/357

OTHER PUBLICATIONS

Brown et al., J. Am. Chem. Soc., vol. 108, pp. 2049-2054 (1986).
Shibata et al., Heterocycles, vol. 24, pp. 1331-1346 (1986).
Boger, J. Org. Chem., vol. 46, pp. 1208-1210 (1981).
Jones et al., Can. J. Chem., vol. 59, pp. 1574-1579 (1981).

*Primary Examiner*—Mark L. Berch
*Attorney, Agent, or Firm*—Peter C. Richardson; J. Trevor Lumb; D. Stuart McFarlin

[57] ABSTRACT

Diastereomeric 5R,6S-6-(1R-hydroxyethyl)-2-(1S-oxo-3R-thiolanylthio)-2-penem-3-carboxylic acid and 5R,6S-6-(1R-hydroxyethyl)-2-(1R-oxo-3S-thiolanylthio)-2-penem-3-carboxylic acid, and pharmaceutically-acceptable salts and in vivo hydrolyzable esters thereof, useful as systemic antibacterial agents; and intermediates and processes which are useful in the said synthesis of said diastereoisomers.

5 Claims, No Drawings

DIASTEREOMERIC 5R,6S-6-(1R-HYDROXYETHYL)-2-(CIS-1-OXO-3-THIOLANYLTHIO)-2-PENEM-3-CARBOXYLIC ACIDS

This is a division of application Ser. No. 07/460,118, filed on Oct. 18, 1989, U.S. Pat. No. 5,013,729.

BACKGROUND OF THE INVENTION

The present invention is directed to antibacterial compounds which are diastereomeric 5R,6S-6-(1R -hydroxyethyl)-2-(cis-1-oxo-3-thiolanylthio)-2-penem-3-carboxylic acids, viz., the 2-(1S-oxo-3R-thiolanylthio) variant of the formula (I) below, and the 2-(1R-oxo-3S-thiolanylthio) variant of the formula (II) below; the pharmaceutically-acceptable salts and in vivo hydrolyzable esters thereof; and intermediates and processes useful in the preparation of said diastereoisomers.

Antibacterial 5R,6S-6-(1R-hydroxyethyl)-2-(cis-1-oxo-3-thiolanylthio)-2-penem-3-carboxylic acid, which is a diastereomeric mixture of two compounds, was earlier disclosed as a valuable antibacterial substance by Hamanaka, U.S. Pat. No. 4,619,924 and European patent application 130,025. Although detectable by analytical methods, the pure diastereomeric compounds of assigned structure have heretofore been unavailable. Disclosure of an improved process for that diastereomeric mixture from racemic cis-3-(acetylthio)thiolane 1-oxide, which employs mixed diastereomeric intermediates otherwise analogous to those presently used, will be found in a European patent application by Volkmann et al., scheduled for publication on May 27, 1987 under the No. 223,397.

Concerning the present optically active precursors, Brown et al., J. Am. Chem. Soc., vol. 108, pp. 2049-2054 (1986) have reported the synthesis of (S)-3-hydroxythiolane [inadvertently depicted as the (R)-isomer, but actually of configuration opposite to that of the present (R)-3-hydroxythiolane, of the formula (XI) below] by asymmetric hydroboration of 2,3-dihydrothiophene. Partial enzymic oxidation of racemic 3-hydroxythiolane by Jones et al., Can. J. Chem., vol. 59, pp. 1574-1579 (1981) permitted recovery of 3-hydroxythiolane containing the (R)-isomer in slight excess. Present optically active precursors (R)-(2-methanesulfonyloxyethyl)oxirane [of the formula (XIII) below wherein $R^9=CH_3$] and (S)-2-bromo-1,4-di(methanesulfonyloxy)butane [of the formula (Xa) below wherein $R^8=CH_3$] are known compounds; both preparable according to Shibata et al., Heterocycles, vol. 24, pp. 1331-1346 (1986); the former also according to Boger et al., J. Org. Chem., vol. 46, pp. 1208-1210 (1981).

SUMMARY OF THE INVENTION

We have now discovered methods for preparing the diastereomeric penem compounds, 5R,6S-6-(1R-hydroxyethyl)-2-(1S-oxo-3R-thiolanylthio)-3-carboxylates, of the absolute stereochemical formula

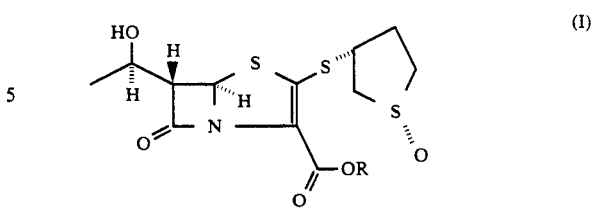

and 5R,6S-6-(1R-hydroxyethyl)-2-(1R-oxo-3S -thiolanylthio)-3-carboxylates, of the absolute stereochemical formula

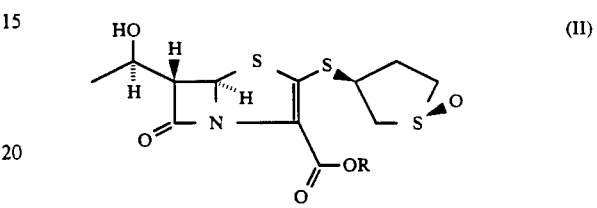

wherein R is hydrogen or a radical forming an ester hydrolyzable under physiological conditions; and the pharmaceutically-acceptable cationic salt thereof when R is hydrogen.

Because each of these compounds, and their several immediate precursors, are single, homogeneous compounds, the quality of the final products is much better controlled relative to the previously reported diastereomeric mixture of these compounds, an important factor in clinical use. Based on in vitro studies of the presently isolated compounds (I) and (II), both show about the same intrinsic antibacterial activity. However, it is surprising that, in the form of their pivaloyloxymethyl esters, the isomer of the formula (II) is better absorbed orally than the isomer (I); and, evidently as a result of a lowered level of metabolic destruction, the isomer (II) shows virtually twice the urine recovery as the isomer (I) whether administered parenterally as the sodium salt or orally as the pivaloyloxymethyl ester. For these reasons, the present pure diastereoisomers are preferred over the earlier diastereomeric mixture, and the isomers of the formula (II) are most preferred.

Said pharmaceutically-acceptable cationic salts include, but are not limited to, those of sodium, potassium, calcium, N,N'-dibenzylethylenediamine, N-methylglucamine (meglumine) and diethanolamine. The preferred cationic salts are those of potassium and sodium.

The reference to esters which are hydrolyzable under physiological conditions refers to those esters frequently referred to as "pro-drugs." Such esters are now as well-known and common in the penicillin art as pharmaceutically-acceptable salts. Such esters are generally used to enhance oral absorption, but in any event are readily hydrolyzed in vivo to the parent acid. The more preferred ester forming radicals are those wherein R is:
 (5-methyl-1,3-dioxol-2-on-4-yl)methyl;
 1H-isobenzofuran-3-on-1-yl;
 gamma-butyrolacton-4-yl;
 —CHR$^1$OCOR$^2$; or
 —CHR$^1$OCOOR$^3$;
wherein $R^1$ is hydrogen or methyl; $R^2$ is $(C_1-C_6)$alkyl, $(C_1-C_6)$carboxyalkyl, carboxycyclohexyl or carboxyphenyl; and $R^3$ is $(C_1-C_6)$alkyl. The most preferred radicals are pivaloyloxymethyl and 1-(ethoxycarbonyloxy)ethyl.

The present invention is also directed to intermediate compounds of the absolute stereochemical formulas

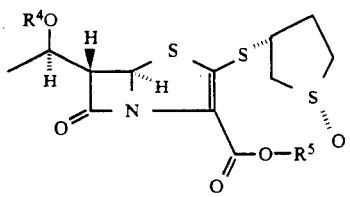

(III)

and

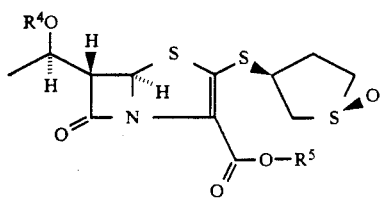

(IV)

wherein $R^4$ is hydrogen or a conventional silyl hydroxy protecting group, preferably t-butyldimethylsilyl; $R^5$ is hydrogen, —$CH_2$—CX=$CH_2$, or —$CH_2$—O—CO—C(CH_3)_3$ (with the proviso that $R^5$ is —$CH_2$—CX=$CH_2$ when $R^4$ is hydrogen); and X is hydrogen or chloro, preferably chloro; or a salt thereof when $R^5$ is hydrogen;

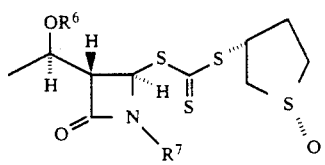

(V)

and

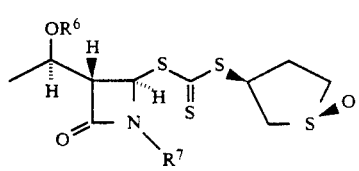

(VI)

wherein $R^6$ is said conventional silyl protecting group; $R^7$ is hydrogen or

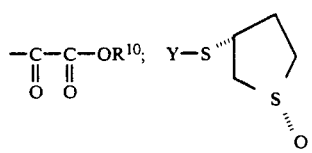

(VII)

and

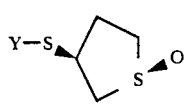

(VIII)

wherein $R^{10}$ is —$CH_2$—CX=$CH_2$ or —$CH_2$—O—CO—C(CH_3)_3$, X is hydrogen or chloro, Y is $CH_3CO$, $M^\oplus$, or $M^\oplus$

and $M^\oplus$ is an alkali metal cation, preferably $Na^\oplus$; and

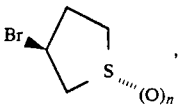

(IX)

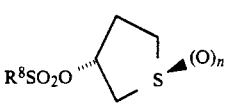

(X)

and

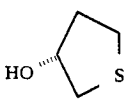

(XI)

wherein $R^8$ is $(C_1-C_3)$alkyl, phenyl or tolyl, preferably the latter, and n is 0 or 1.

The present invention is further directed to:

(1) a process for the preparation of a compound of the absolute stereochemical formula

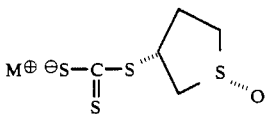

(VIIa)

wherein $M^\oplus$ is an alkali metal cation, preferably $Na^\oplus$, which comprises the steps of:

(a) conventional cyclization of a compound of the absolute stereochemical formula

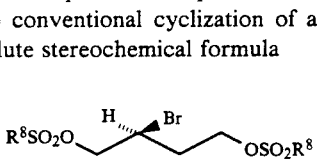

(XII)

wherein $R^8$ is $(C_1-C_3)$alkyl, phenyl or p-tolyl (preferably methyl) with an alkali metal sulfide in a reaction-inert solvent to form a compound of the absolute stereochemical formula

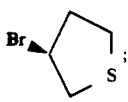

(IXa)

(b) conventional oxidation of the compound of the formula (IXa) with substantially one equivalent of oxidant in a reaction-inert solvent to form a compound of the absolute stereochemical formula

 (IXb)

(c) conventional nucleophilic displacement of bromo in the compound of the formula (IXb) with an alkali metal thioacetate in a reaction-inert solvent to form a compound of the absolute stereochemical formula

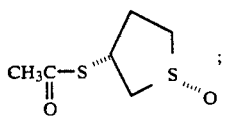 (VIIb)

and (d) conventional conversion of the compound of the formula (VIIb), by the action fo the CS$_2$ and an alkali metal (C$_1$-C$_3$)alkoxide, preferably sodium ethoxide, in a reaction-inert solvent, to form said compound of the formula (VIIa);

(2) a process for the preparation of a compound of the absolute stereochemical formula

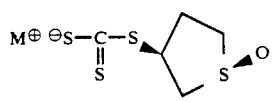 (VIIIa)

wherein M$^\oplus$ is an alkali metal cation, preferably Na$^\oplus$, which comprises the steps of:

(a) conversion of an epoxide of the absolute stereochemical formula

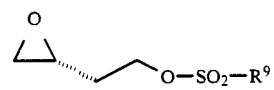 (XIII)

wherein R$^9$ is (C$_1$-C$_3$)alkyl, phenyl or p-tolyl, preferably methyl, by the action of an alkali metal sulfide in a reaction-inert solvent to form a compound of the absolute stereochemical formula

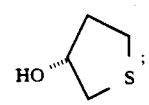 (XI)

(b) conventional sulfonylation of the compound of the formula (XI) in a reaction-inert solvent to form a compound of the absolute stereochemical formula

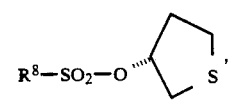 (Xa)

wherein R$^8$ is (C$_1$-C$_3$)alkyl, phenyl or tolyl, preferably the latter;

(c) conventional oxidation of the compound of the formula (Xa) in a reaction-inert solvent to form a compound of the absolute stereochemical formula

 (Xb)

(d) conventional nucleophilic displacement of R$^8$—SO$_2$—O in the compound of the formula (Xb) with an alkali metal thioacetate in a reaction-inert solvent to form a compound of the absolute stereochemical formula

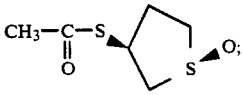 (VIIIb)

and (e) conventional conversion of the compound of the formula (VIIIb), by the action of CS$_2$ and an alkali metal alkoxide, preferably sodium ethoxide, in a reaction-inert solvent, to form said compound of the formula (VIIIa); and (3) an improved process for the preparation of a compound of the absolute stereochemical formula

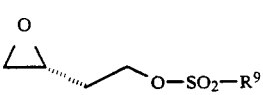 (XIII)

wherein R$^9$ is (C$_1$-C$_3$)alkyl, phenyl or p-tolyl, preferably methyl, which comprises the steps of (a) reacting a compound of the absolute stereochemical formula

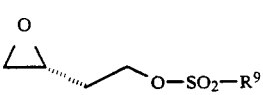 (XIV)

with Cs$_2$CO$_3$ in a reaction-inert solvent to form a compound of the absolute stereochemical formula

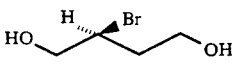 (XV)

in greater than 90% stoichiometric step yield; and (b) sulfonylation of the compound of the formula (XV) with a sulfonyl chloride of the formula R$^9$—SO$_2$—Cl in the presence of a tertiary amine in a reaction-inert solvent to form said compound of the formula (XIII) in greater than 90% yield.

As used herein, the expression "reaction-inert solvent" refers to a solvent which does not interact with starting materials, reagents, intermediates or products in a manner which adversely affects the yield of the desired product.

DETAILED DESCRIPTION OF THE INVENTION

The individual diastereomeric compounds of the present invention are now readily prepared. An important feature of the present invention is the preparation of the optically active precursors of the above formulas (VII) and (VIII) from the known optically active compounds of the formulas (XII) and (XIII), respectively.

To prepare the compound (VIIa), the compound of the formula (XII) [known when $R^8$=methyl; prepared analogously when $R^8$ is other than methyl] is first reacted with an alkali metal sulfide (suitably $Na_2S \cdot 9H_2O$), to form (S)-3-bromothiolane (IXa). At least one molar equivalent, usually a slight (e.g., 5–10%) excess of the sulfide salt is used, together with reaction-inert solvent, suitably an aqueous solvent such as an aqueous ($C_1$–$C_3$-)alkanol (e.g., aqueous methanol) or aqueous acetonitrile. Temperature is not critical, e.g., 0°–60° C. being generally satisfactory. Ambient temperatures, e.g., 17°–28° C., are particularly convenient, avoiding the cost of heating and cooling, although more elevated temperatures have the advantage of reducing the time necessary to complete the reaction.

The intermediate bromothiolane (IXa) is then conventionally oxidized to the S-oxide (IXb), using substantially one molar equivalent of oxidant (usually in slight excess to achieve complete mono-oxidation, without significant oxidation to the dioxide). Suitable oxidants are m-chloroperbenzoic acid and potassium peroxymonosulfate [$KHSO_5 \cdot (KHSO_4)_{\frac{1}{2}} \cdot (K_2SO_4)_{\frac{1}{2}}$]. The oxidation is carried out in a reaction-inert solvent, $CH_2Cl_2$ being particularly well-suited for the perbenzoic acid, and acetone for the peroxymonosulfate. Temperature is not critical, e.g., temperatures of −10° to 40° C. being generally satisfactory. It is convenient to combine the reagents at reduced temperature, e.g., 0°–5° C., then allow the reaction to proceed to completion at ambient temperature as defined above.

The intermediate sulfoxide (IXb) is then reacted with an alkali metal thioacetate under conventional nucleophilic displacement conditions to form 3R-(acetylthio)-thiolane 1S-oxide (VIIb). Usually an excess (e.g., 1.5–2 molar equivalents) of the thioacetate salt is employed in a reaction-inert solvent which will permit appreciable concentrations of both reactants in order to drive this bimolecular reaction to completion within a reasonable period of time. In the present case, acetone is a particularly well suited solvent. Temperature is not critical, e.g., 30°–100° C. being generally satisfactory, the reflux temperature of solvent acetone being eminently satisfactory.

Finally, the acetylthiolane (VIIb) is converted, via the mercaptide salt (VII, $Y=M^\oplus$), to the trithiocarbonate salt (VIIa). The intermediate mercaptide salt is generally formed in situ by the action of an alkali metal alkoxide, usually in the corresponding alkanol as the reaction-inert solvent, sodium methoxide/methanol, sodium ethoxide/ethanol and sodium isopropoxide/isopropanol all being well suited for the purpose, usually at reduced temperature, e.g., −15° to +15° C., conveniently near 0° C. Once formed, the mercaptide salt is usually reacted without isolation with at least one molar equivalent of carbon disulfide (usually in excess, e.g., 3–5 molar equivalents), usually at even lower temperature, e.g., −40° to 0° C., to form the desired 3R-(thio(-thiocarbonyl)thio)thiolane 1S-oxide of the formula (VIIa). The latter is isolated by conventional methods or alternatively used in situ in the next process step.

To prepare the compound (VIIIa) the epoxide of the formula (XIII) [known when $R^8$=methyl; in any event prepared according to the improved method disclosed elsewhere herein] is first reacted with an alkali metal sulfide, under conditions as disclosed above for the conversion of (XII) to (IXa), in this case forming (R)-3-hydroxythiolane of the formula (XI). The latter is converted to the alkane-, benzene- or p-toluenesulfonate of the formula (Xa) under conventional conditions, e.g., using substantially one molar equivalent of the corresponding sulfonyl chloride, $R^8SO_2Cl$, in the presence of at least one molar equivalent of a tertiary amine, preferably p-dimethylaminopyridine, in a reaction-inert solvent such as methylene chloride in a non-critical temperature range of 0°–50° C., suitably at ambient temperature as defined above. The compound (Xa) is then oxidized to the sulfoxide (Xb), the sulfonate group nucleophilically displaced with thioacetate to form 3S-(acetylthiothiolane 1R-oxide, of the formula (VIIIb), hydrolyzed to the mercaptide (VIII, $Y=M^\oplus$) and finally reacted with $CS_2$ to form the trithiocarbonate (VIIIa), all under the conditions noted above for the corresponding stepwise conversion of (IXa) to (VIIa).

The present improved two-step process for precursor (R)-(2-methanesulfonyloxyethyl)oxirane of the above formula (XIII) employs ($Cs_2CO_3$) in a reaction-inert solvent (e.g., $CH_2Cl_2$) at ambient temperature [in place of the refluxing aqueous NaOH of Shibata et al., cited above], thus producing, after conventional sulfonylation, said compound (XIII) having much higher optical rotation.

The second precursor required for the synthesis of the above compounds of the formulas (I) and (II) is 3R,4R-4-acetoxy-3-[1R-1-(silyl protected hydroxy)ethyl]-2-azetidinone, of the formula

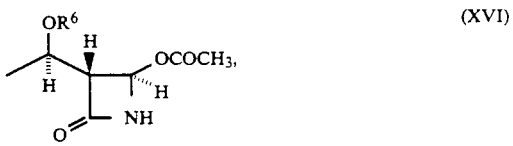

(XVI)

where $R^6$ is a conventional silyl hydroxy protecting group (preferably dimethyl-t-butylsilyl), a compound which is efficiently prepared from 6-aminopenicillanic acid, e.g., by the method of Leanza et al., *Tetrahedron*, vol. 39, pp. 2505–2513 (1983). Thus, in the next stage of the synthesis, the azetidinone (XVI) is converted to the diastereomeric compound of the formula (V) or (VI) wherein $R^6$ is hydrogen, by reaction with the trithiocarbonate (VIIa) or (VIIIa), respectively. With or without isolation of said trithiocarbonate, the reactants are combined in a reaction-inert solvent, such as a ($C_1$–$C_3$)alkanol, e.g., isopropanol, conveniently in the same solvent as that used for preparation of the trithiocarbonate, in the presence of excess carbon disulfide (which can be already present in situ from the preceding step). The reaction is generally carried out at reduced temperature, e.g., ±20° C., conveniently at ice bath temperature (0°–5° C.).

The compound of the formula (V) or (VI) wherein $R^7$ is hydrogen is then reacted with an acid fluoride of the formula

(XVII)

wherein $R^{10}$ is as defined above, to form the corresponding compound (V) or (VI) wherein $R^7$ is —COCOOR$^{10}$. This step is carried out in a reaction-inert solvent at 0° to −80° C. in the presence of a tertiary amine. Lower temperatures, e.g., −30° to −70° C., are preferred. A preferred reaction-inert solvent is methylene chloride. A preferred tertiary amine is N,N-diisopropylethylamine.

In the next step of the synthesis, the penem compound of the formula (III) or (IV) wherein $R^4$ is a silyl-protecting group and $R^5$ corresponds to $R^{10}$, is formed by the action of a trialkyl phosphite (e.g., triethyl phosphite) on a compound of the formula (V) or (VI) wherein $R^7$ is —COCOOR$^{10}$. This step is also carried out in a reaction-inert solvent (e.g., ethanol-free chloroform). Temperature is not critical, but will generally be above ambient, e.g., 40° to 80° C., conveniently reflux temperature when chloroform is the solvent.

In the final or penultimate step, the silyl-protecting group is removed by standard methods, e.g., in the case of the dimethyl-t-butylsilyl, by the action of acetic acid and tetrabutylammonium fluoride in anhydrous tetrahydrofuran, to form the compound of the formula (I) or (II) in the form of its pivaloyloxymethyl ester or of the formula (III) or (IV) wherein $R^4$ is hydrogen and $R^5$ is —$CH_2$—CX=$CH_2$.

Finally, when $R^5$ is allyl or 2-chloroallyl, the ester is hydrolyzed to produce the desired penem of the formula (I) or (II), above, in the form of the acid or its pharmaceutically-acceptable cationic salt. Anhydrous conditions are generally employed to avoid any possible degradation of the beta-lactam. Preferred conditions employ 1 to 1.1 molar equivalents of an alkali metal salt of a lipophilic carboxylic acid (e.g., sodium 2-ethylhexanoate) in an anhydrous reaction-inert solvent (e.g., methylene chloride and/or ethyl acetate) in the presence of catalytic amounts of triphenylphosphine and tetrakis(triphenylphosphine)palladium (e.g., about 0.15 molar equivalents of the former and about 0.075 molar equivalents of the latter). Although temperature is not critical, the reaction is conveniently carried out at ambient temperature. With these reagents, the compound of the formula (I) or (II) is usually initially isolated in the form of its alkali metal (e.g., sodium) salt. If desired, the salt is converted to the free acid form, during or after isolation, by standard methods, e.g., acidification of an aqueous solution of the salt, with extraction of the free acid into a water immiscible organic solvent.

Other pharmaceutically-acceptable cationic salts of the present invention are also readily prepared by standard methods. For example, an equivalent of the corresponding cationic hydroxide, carbonate or bicarbonate or of an amine, is combined with the carboxylic acid in an organic or aqueous solvent, preferably at reduced temperature (e.g., 0°–5° C.), with vigorous agitation and slow addition of the base. The salt is isolated by concentration and/or the addition of a non-solvent.

The compounds of the formula (I) or (II) wherein R represents an in vivo hydrolyzable ester are also prepared from the corresponding free acids or cationic salts according to known methods, readily identified by those skilled in the penicillin art (see for example, U.S. Pat. Nos. 3,951,954; 4,234,579; 4,287,181; 4,342,693; 4,452,796; 4,342,693; 4,348,264; 4,416,891; and 4,457,924). In the present instance, the preferred precursors are hydroxy protected compounds of the formula (III) or (IV) wherein $R^4$ is a silyl protecting group, preferably dimethyl-t-butylsilyl, and $R^5$ is hydrogen or a salt, preferably the tetrabutylammonium salt. These precursors are obtained by selective hydrolysis of the corresponding allyl or 2-chloroallyl esters by the special method described above. The resulting alkali metal salt is preferably converted to the tetrabutylammonium salt prior to reacting with the ester forming reagent, e.g., chloromethyl pivalate or 1-chloroethyl ethyl carbonate. Preferred methods of ester formation are exemplified below. The silyl protecting group in the intermediate compounds is then removed to produce the desired compounds of the formula (I) or (II) wherein R is a radical forming an in vivo hydrolyzable ester.

The required acid fluorides (XVII) are prepared from the corresponding acid chlorides using reagents previously used for this purpose, either anhydrous cesium fluoride (usually at or near ambient temperature, with reagents initially combined at lower temperature, e.g., 0° to −30° C.), or potassium fluorosulfinate (FSO$_2$K, usually at warmer temperatures, e.g., 45°–85° C.). The latter reagent and conditions are preferred when $R^5$ is pivaloyloxymethyl.

Concerning other starting materials required for the process of the present invention, 3R,4R-4-acetoxy-3-[1R-1-(silyloxy)ethyl]-2-azetidinones are readily available according to the method of Leanza et al., cited above; allyl oxalochloride is available according to the method of Afonso et al., *J. Am. Chem. Soc.*, vol. 104, pp. 6138–6139 (1982); 2-chloroallyl oxalochloride is available from 2-chloroallyl alcohol and oxalyl chloride according to the method detailed below; and pivaloyloxymethyl oxalochloride is prepared by a series of steps from benzyl half ester of oxalic acid and chloromethyl pivalate, also detailed below.

The pure diastereomeric, antibacterial compounds of the formulas (I) and (II) are tested, formulated and used according to methods detailed in above cited Hamanaka, U.S. Pat. No. 4,619,924, hereby incorporated by reference. Within the human dosage ranges there disclosed, the more preferred dosage range for the present compounds (I) and (II) is 10–80 mg/kg/day both orally and parenterally. These FIGURES are illustrative only, since in some circumstances the attending physician will find it more beneficial to employ dosages outside of these ranges. In vivo hydrolyzable esters, particularly the pivaloyloxymethyl and 1-(ethoxycarbonyloxy)ethyl esters, are preferred in oral use, while the sodium or potassium salts are particularly preferred for parenteral use.

The following examples are given by way of illustration and are not to be construed as limitations of this invention, many variations of which are possible within the scope and spirit thereof.

EXAMPLE 1

(R)-3-Hydroxythiolane (XI)

In a dry flask under $N_2$, 19.62 g (0.118 mol) of (R-(2-methanesulfonyloxyethyl)oxirane was dissolved in 600 ml acetonitrile and 100 ml water. Sodium sulfide (18.67 g, 0.239 mol) was added and the reaction mixture stirred at room temperature for 24 hours. The two layers were separated and the aqueous layer extracted with methylene chloride (3×15 ml). The combined organic layers were washed with 1N sodium hydroxide. The aqueous layer was extracted with methylene chloride (3×150 ml), salted with NaCl, and extracted with an additional 2×100 ml of $CH_2Cl_2$. All organic layers were combined, washed with 50 ml 1N NaOH, 50 ml of saturated NaCl, dried (MgSO$_4$) and stripped to yield title product, 11.05 g (90% step yield, 90% over-all yield from the S-2-bromo-1,4-butanediol); [alpha]$_D$=+13.93° (c=1.4,CHCl$_3$); pnmr(CDCl$_3$)delta(ppm): 1.70–1.90 (1H, m, CH), 2.00–2.18 (2H, m, CH, OH), 2.70–2.98

(4H, m, CH$_2$S), 4.50–4.52 (1H, m, CHO). For the corresponding S-isomer, Brown et al., *J. Am. Chem. Soc.*, vol. 108, p. 2049 (1986) reported [alpha]$^{25}_D$ = −14.5 (c=1, CHCl$_3$).

EXAMPLE 2

(R)-3-(p-Toluenesulfonyloxy)thiolane (Xa, R$^8$=p-tolyl)

In a flame-dried flask under nitrogen, 11.03 g (0.106 mol) (R)-3-hydroxythiolane was dissolved in 150 ml dry methylene chloride and cooled to −5° C. To this was added 25.88 g (0.212 mol) 4-dimethylaminopyridine and 20.19 g (0.106 mol) p-toluenesulfonylchloride and the mixture stirred at room temperature for 60 hours. It was then washed with 1N hydrochloric acid (25 ml), the wash extracted with methylene chloride (3×50 ml), the combined organic layers washed with brine, dried (MgSO$_4$) and evaporated to dryness to provide 34.73 g crude product. This was filtered through a silica gel pad (5 inch diameter, 4 inches deep), eluting with 1:5 ethyl acetate:hexane, then ethyl acetate alone. The product-containing fractions were combined and evaporated to yield 21.52 g (79%) purified product; [alpha]$_D$ = +16.76° (c=2.98,CHCl$_3$); pnmr(CDCl$_3$)delta(ppm): 1.76–1.90 (1H, m, CH), 2.12–2.26 (1H, m, CH), 2.40 (3H, s, CH$_3$), 2.70–3.00 (4H, m, CH$_2$S), 5.13–5.16 (1H, m, CHO), 7.25 (2H, d, CH), 7.74 (2H, d, CH).

EXAMPLE 3

3R-(p-Toluenesulfonyloxy)thiolane 1R-Oxide (Xb, R$^8$=tolyl)

A solution of 46.30 g (0.179 mol) 3R-(toluenesulfonyloxy)thiolane in 600 ml acetone, under nitrogen was cooled to 0° C. In a separate flask 61.73 g (0.100 mol) potassium peroxymonosulfate (2 KHSO$_5$·KHSO$_4$·K$_2$SO$_4$;) was stirred in 500 ml distilled water until clear. This was added to the acetone solution at 0° C. and the mixture allowed to warm to room temperature. After 25 minutes 75 ml of 10% (w/v) aqueous sodium sulfite was added, the acetone was evaporated, 300 ml ethyl acetate added and the aqueous layer was extracted with ethyl acetate (3×100 ml). The combined extracts were dried (MgSO$_4$) and concentrated to dryness to yield 48.57 g of crude product. The latter was purified by silica gel chromatography using 10:10:1 ethyl acetate:CH$_2$Cl$_2$:CH$_3$OH as eluant to afford purified title product, 34.67 g (71%); [alpha]$_D$ = +4.26° (c=3.0, CHCl$_3$).

EXAMPLE 4

3S-(Acetylthio)thiolane 1R-Oxide (VIIIb)

In a flame-dried flask under nitrogen, 31.67 g (0.1156 mol) 3R-(p-toluenesulfonyloxy)thiolane 1R-oxide was dissolved in 300 ml acetone and 19.81 g (0.1734 mol) potassium thioacetate was added. The mixture was heated at reflux for 3.5 hours and allowed to stir at room temperature overnight. The mixture was filtered, rinsed and washed with 500 ml acetone and the filtrate and washings were evaporated in vacuo to obtain 23.96 g of the desired product as an oil. The oil was purified by flash chromatography on a 120 mm×25 cm silica gel column eluting with 19:1 ethyl acetate:methanol collecting 125 ml fractions. Fractions 42–64 were combined and stripped to yield purified title product as an oil which crystallized on standing, 16.46 g; (80%); m.p. 51°–52° C.; [alpha$_D$ = −83.41° (c=0.86, CHCl$_3$).

Analysis calculated for C$_6$H$_{10}$S$_2$O$_2$: C, 40.4; H. 5.6%; Found: C, 40.15; H, 5.53%.

EXAMPLE 5

Sodium 3S-(Thio(thiocarbonyl)thio)thiolane 1R-Oxide (VIIIa, M$^\oplus$=N$^\oplus$)

In a flame-dried flask under nitrogen, a solution of 1.78 g (10 mmol) 3S-(acetylthio)thiolane 1R-oxide in 6 ml ethanol was cooled to −5° C. Sodium ethoxide (21% by weight in ethanol, 3.73 ml, 10 mmol) was added and the mixture stirred at −5° C. for 30 minutes, then cooled to −20° C., 3.0 ml (50 mmol) carbon disulfide added and stirring continued for 30 minutes. To this was added 75 ml anhydrous tetrahydrofuran. The resulting mixture was stirred for a few minutes, seeded with crystals of the title compound, cooled and held at 15° C., and stirred until crystallization was complete. The mixture was filtered, washed with cold tetrahydrofuran and then with ethyl ether. The resulting crystals were air-dried under nitrogen to afford 2.10 g of title product, solvated with 0.5 molar equivalents of tetrahydrofuran. Another 592 mg was recovered by reworking the mother liquor; m.p. 120°–121° C. (dec.), blackens at 155°–156° C.; [alpha]$_D$ = −79.52° (c=0.05, in H$_2$O).

EXAMPLE 6

3S,4R-3-[1R-1-(Dimethyl-t-butylsilyloxy)ethyl]-4-[1R-oxo-3S-thiolanylthio(thiocarbonyl)thio]-2-azetidinone (VI, R$^7$=H, R$^6$=Me$_2$tBuSi)

In a flame-dried flask under N$_2$, a solution of 3R,4R-4-acetoxy-3-[1R-(dimethyl-t-butylsilyloxy)ethyl]-2-azetidinone [1.87 g, 6.5 mmol; Leanza et al., *Tetrahedron* 39, pp. 2505–2513 (1983)] in 20 ml isopropyl alcohol and CS$_2$ (0.15 ml, 2.5 mmol) were combined and cooled to 3° C. The product of the preceding Example (1.36 g, 5 mmol) was added portionwise, maintaining 3° C. After 0.5 hour at 3° C., the reaction was quenched with 40 ml saturated ammonium chloride solution, and then 50 ml ethyl acetate was added. The organic layer was separated and the aqueous layer was extracted with an additional 2×25 ml ethyl acetate. The combined ethyl acetate layers were washed 2×20 ml H$_2$O and 2×20 ml 20% CaCl$_2$, dried over MgSO$_4$, filtered and concentrated in vacuo to yield crude title product, 3.04 g. The latter was dissolved in about 2 ml acetone, isopropyl ether was added dropwise until precipitation of solid started, the mixture was stirred for one hour, then 120 ml petroleum ether was added rapidly with stirring. The resulting solid was collected by filtration, air-dried, then dried in vacuo, and finally chromatographed on silica gel using 19:1 ethyl acetate:methanol as eluant to yield 1.35 g (61%) of purified title product. Recrystallization from 4 ml acetone by the same procedure gave back 1.15 g of product; [alpha]$_D$ = +109.36° (c=0.20, CHCl$_3$); pnmr(CDCl$_3$)(delta)(ppm) 300 MHz: 0.05 (s, 3H), 0.86 (s, 9H), 1.18 (s, 3H), 1.74 (s, 2H), 2.68 (m, 3H), 2.82 (m, 1H), 3.17 (m, 2H), 3.74 (q, 1H), 4.25 (t, 1H), 4.52 (t, 1H), 5.61 (s, 1H), 6.52 (s, 1H), 7.20 (s, 1H).

EXAMPLE 7

3S,4R-N-[(2-Chloroallyloxy)oxalyl]-3-[1R-(dimethyl-t-butylsilyloxy)ethyl]-4-[1R-oxo-3S-thiolanylthio(thiocarbonyl)thio]-2-azetidinone (VI, R$^6$=Me$_2$tBuSi, R$^7$=COCOOCH$_2$CClCH$_2$)

A flame-dried, three-neck flask equipped with a dropping funnel and low temperature thermometer under a $N_2$ atmosphere was charged with the product of the preceding Example (878 mg, 2 mmol) and 15 ml dry methylene chloride (passed through neutral alumina). The reaction was cooled to $-50°$ to $-55°$ C. internal temperature and N,N-diisopropylethylamine (0.45 ml, 2.6 mmol) was added, keeping the temperature less than 50° C. Then 2-chloroallyl oxalofluoride (0.34 ml, 2.6 mmol) was added as fast as possible, again keeping the temperature below 50° C., and the reaction stirred an additional 50 minutes at $-50°$ to $-55°$ C. The reaction was quenched with 15 ml $H_2O$, allowed to warm to 0° C. and diluted with 20 ml fresh $CH_2Cl_2$. The organic layer was separated, washed $1 \times 15$ ml $H_2O$, $1 \times 20$ ml pH 7 buffer and $1 \times 25$ ml saturated NaCl, dried over $MgSO_4$, filtered and concentrated in vacuo to yield 1.05 g of title product as a yellow foam, all of which was used directly in the next step.

EXAMPLE 8

2-Chloroallyl 5R,6S-6-[1R-(Dimethyl -t-butylsilyloxy)ethyl]-2-(1R-oxo -3S-thiolanylthio)-2-penem-3-carboxylate (IV, $R^4 = Me_2tBuSi$, $R^5 = CH_2CClCH_2$)

A flame-dried, three-neck flask equipped with a condenser and an equilibrating addition funnel under a $N_2$ atmosphere was charged with the product of the preceding Example (1.05 g, 2 mmol) and 80 ml ethanol-free chloroform. The reaction was heated to a gentle reflux and triethyl phosphite (0.74 ml, 48 mmol) in 10 ml ethanol-free chloroform was added dropwise over a ten-hour period. The reaction was heated at a gentle reflux for an additional ten hours. The reaction was cooled to room temperature and concentrated in vacuo. The residue was dissolved in 5 ml ethyl acetate. Isopropyl ether (40 ml) was added dropwise with stirring as crystallization began. Finally, 40 ml petroleum ether was added dropwise, the mixture filtered and solids dried to yield 0.47 g (44%) of the product; m.p. 140°-141° C.; [alpha]$_{D}$ = +36.78° (c=0.5, CHCl$_3$).

EXAMPLE 9

2-Chloroallyl 5R,6S-6-(1R-Hydroxyethyl)-2-(1R-oxo-3S-thiolanylthio)-2-penem-3-carboxylate (IV, $R^4$ = H, $R^5 = CH_2CClCH_2$)

A flame-dried, three-neck flask equipped with a thermometer and two addition funnels under a $N_2$ atmosphere was charged with the product of the preceding Example (0.25 g, 0.46 mmol) and 0.5 ml dry tetrahydrofuran. To the stirred reaction was added glacial acetic acid (0.26 ml, 4.6 mmol), followed by tetrabutyl ammonium fluoride in tetrahydrofuran (IM, 1.38 ml). The resulting solution was stirred sixteen hours at room temperature, diluted with 15 ml ethyl acetate and 4 ml water, adjusted to pH 6.4 with potassium acetate, the layers separated, and the organic layer washed $3 \times 3$ ml water. The latter were combined and back-washed $3 \times 3$ ml $CH_2Cl_2$. The combined organic layers (ethyl acetate and $CH_2Cl_2$) were dried over $Na_2SO_4$, filtered and concentrated in vacuo to yield crude product, 0.46 g. The crude was taken up in 25 ml ethyl acetate and washed $3 \times 6$ ml $H_2O$. The organic layer was dried over $Na_2SO_4$, filtered and stripped to yield purified title product, 88 mg; m.p. 177°-178° C.; [alpha]$_{D}$ = +45.28° (c=0.25 in dimethylsulfoxide).

EXAMPLE 10

Sodium 5R,6S-6-(1R-Hydroxyethyl)-2-(1R-oxo-3S -thiolanylthio)-2-penem-3-carboxylate (II, R=Na)

A flame-dried flask wrapped in aluminum foil, under $N_2$, was charged with the product of the preceding Example (3.60 g, 8.5 mmol) in 115 ml of degassed $CH_2Cl_2$, followed by triphenylphosphine (0.72 g, 2.75 mmol), sodium 2-ethylhexanoate (6.72 ml of 1.39M in ethyl acetate, 9.34 mmol) and tetrakis(triphenylphosphine)palladium (0.72 g, 0.62 mmol). The reaction was stirred at room temperature for fifty minutes, an additional 72 mg each of triphenylphosphine and tetrakis(triphenylphosphine)palladium were added and the reaction stirred at room temperature an additional twenty minutes. Hplc purity ethyl acetate (150 ml) was added to the reaction over a fifteen minute period. The reaction was filtered and the solids air-dried to yield crude product, 4.07 g. The latter was slurried with 45 ml ethyl acetate for 45 minutes, filtered and dried to afford 3.96 g of still crude product. The latter was taken up in 70 ml of water, treated with activated carbon, filtered and the filtrate freeze-dried to yield title product, 2.63 g.

By the same method, the product of Example 27 below, is converted to the same title product in similar yield.

EXAMPLE 11

5R,6S-6-(1R-1-Hydroxyethyl)-2-(1R-oxo-3S -thiolanylthio)-2-penem-3-carboxylic Acid (II, R=H)

The sodium salt of the preceding Example (2.63 g) was dissolved in 8 ml $H_2O$ and cooled to 0°-5° C. The pH was adjusted to 2.45 with 1N HCl as product began to crystallize. The mixture was stirred at 0°-5° C. for forty-five minutes, filtered, washed with a small amount of $H_2O$ and dried to yield 2.16 g of title product as a white solid; m.p. 135° C. (dec.); [alpha]$_{D}$ = +366.01° (c=1 in dimethylsulfoxide).

EXAMPLE 12

Sterile Sodium 5R,6S-6-(1R-Hydroxyethyl)-2-(1R-oxo-3S -thiolanylthio)-2-penem-3-carboxylate (II, R=Na)

The product of the preceding Example (1.95 g) was suspended in 60 ml $H_2O$ and cooled to 0°-5° C. Maintaining that temperature range and using vigorous stirring, the pH was adjusted from 2.98 to a constant pH of 6.00 by the dropwise addition of NaOH (4.2 ml of 1N, followed by 10.75 ml of 0.1N). The solution was millipore filtered into a sterile flask and freeze-dried (if desired, freeze-dried after subdivision to obtain the desired dosage in rubber-stoppered sterile vials) to yield sterile title product, 1.926 g, which, if not already subdivided, can be subdivided into vials at the desired dosage level. This purified product shows m.p. 158° C. (dec.); [alpha]$_{D}$ = +81.31° (c=1 in $H_2O$).

For parenteral dosage, the sterile sodium salt is dissolved in sterile water for injection.

EXAMPLE 13

Tetrabutylammonium 5R,6S-6-[1R-(Dimethyl-t -butylsilyloxy)ethyl]-2-(1R-oxo-3S-thiolanylthio)-2- penem-3-carboxylate (IV, $R^4 = Me_2tBuSi$, $R^5 = TBA$ salt The product of Example 8 (0.80 g, 1.5 mmol) was reacted according to Example 10 to form intermediate sodium salt in situ. The reaction mixture was diluted with 35 ml ethyl acetate and 4 ml ether, washed 3×10 ml H$_2$O, the organic layer further diluted with 35 ml hexane, and finally washed 3×20 ml H$_2$O. The six aqueous layers were combined, then further combined with tetrabutylammonium hydrogen sulfate (0.51 g, 1.5 mmol) and NaHCO$_3$ (0.25 g, 3 mmol) in 5 ml H$_2$O. After stirring for 15 minutes and salting with Na$_2$SO$_4$, the desired product was extracted into CH$_2$Cl$_2$ (3×90 ml), dried (Na$_2$SO$_4$), treated with activated carbon, filtered and concentrated in vacuo to yield title product, 0.80 g; pnmr(CDCl$_3$)delta(ppm) 300 MHz: 0.05 (s, 6H), 0.85 (s, 9H), 0.99 (t, 12H), 1.28 (d, 3H), 1.30–1.50 (m, 8H), 1.50–1.70 (m, 8H), 2.50–2.82 (m, 4H), 2.96–3.10 (m, 1H), 3.05–3.42 (t, 8H), 3.45–3.62 (m, 2H), 3.80–3.92 (m, 1H), 4.05–4.18 (m, 1H), 5.42 (s, 1H).

EXAMPLE 14

Pivaloyloxymethyl 5R,6S-6-[1R-(Dimethyl-t-butylsilyloxy)ethyl]-2-(1R-oxo-3S-thiolanylthio)-2-penem-3-carboxylate (IV, R$^4$=Me$_2$tBuSi, R$^5$=CH$_2$—O—CO—C(CH$_3$)$_3$ In flame-dried glassware, under N$_2$ the product of the preceding Example (0.80 g, 1.13 mmol) was dissolved in 11 ml acetone. Chloromethyl pivalate (0.25 ml, 1.71 mmol) was added and the mixture stirred 16 hours at room temperature, then stripped in vacuo, finally under high vacuum, to yield title product, 1.05 g; pnmr (CDCl$_3$)delta(ppm) 300 MHz: 0.05 (s, 6H), 0.88 (s, 9H), 1.20 (s, 9H), 1.24 (d, 3H), 2.4–2.6 (m, 4H), 3.05–3.12 (m, 1H), 3.6–3.90 (m, 3H), 4.15–4.28 (m, 1H), 5.59 (s, 1H), 5.81 (q, 2H, J$_{AB}$=12.5 Hz).

The corresponding 1-(ethoxycarbonyloxy)ethyl ester is prepared by the same method, substituting equivalent 1-chloroethyl ethyl carbonate for chloromethyl pivalate.

Title product is alternatively prepared stepwise by the methods of Examples 7–9, substituting equivalent pivaloyloxymethyl oxalofluoride for 2-chloroallyl oxalofluoride in Example 7.

EXAMPLE 15

Pivaloyloxymethyl 5R,6S-6-(1R-hydroxyethyl-2-(1R-oxo-3S-thiolanylthio)-2-penem-3-carboxylate (II, R=CH$_2$—O—CO—C(CH$_3$)$_3$ By the method of Example 9, the product of the preceding Example (0.40 g, 0.69 mmol) was converted to present title product. To isolate, the reaction mixture was diluted with 45 ml ethyl acetate and washed 4×9 ml H$_2$O. The water washes were combined and back extracted 3×9 ml ethyl acetate. All organic layers were combined, washed 2×9 ml saturated NaCl, dried, filtered and concentrated in vacuo, ultimately under high vacuum to yield crude product, 0.28 g. The latter was flash chromatographed on a 40 mm×25 cm column of silica gel, initially eluting with 1:9 ethyl acetate: tetrahydrofuran (50 ml fractions 1–10), and then with tetrahydrofuran for subsequent 50 ml fractions. Fractions 18–44 were combined, evaporated to dryness, and the residue stirred with 70 ml ethyl acetate and filtered to yield purified title product, 0.193 g; pnmr(CDCl$_3$)delta(ppm) 300 MHz: 1.18 (s, 9H), 1.29 (d, 3H, J=6.3 Hz), 2.12 (bs, 1H), 2.6–2.9 (m, 4 Hz), 3.1–3.2 (m, 1H), 3.6–3.90 (m, 3H), 4.20–4.32 (m, 1H), 5.64 (s, 1H), 5.76 (q, 2H, J$_{AB}$=12.5 Hz).

By the same method, the corresponding 1-(methoxycarbonyloxy)ethyl ester of the preceding Example is converted to 1-(ethoxycarbonyloxy)ethyl 5R,6S-6-(1R-hydroxyethyl)-2-(1R-oxo-3S-thiolanylthio)-2-penem carboxylate.

EXAMPLE 16

(S)-3-Bromothiolane (IXa)

To a solution of 97.1 g (0.37 mol) (S)-2-bromo-1,4-di(methanesulfonyloxy)butane in 1400 ml methanol was added over 1 hour a solution of 98.23 g (0.41 mol) sodium sulfide nonahydrate in 500 ml water at 19°–26° C. The mixture was stirred at room temperature for 80 hours. The reaction mixture was diluted with 6 liters methylene chloride, the organic layer separated, washed 2×1 liter H$_2$O, 1×1,500 ml brine, dried (Na$_2$SO$_4$) and the solvent evaporated to provide 36.5 to 46.8 g (59–68%) of crude product as a pale yellow oil. The latter was distilled in vacuo to yield a mobile water clear liquid product, b.p. 32° (0.4 mm), 26.0 g (38% over-all). Alternatively, the crude product (3 g) was flash chromatographed on an 80 mm×15 cm silica gel column using 9:1 hexane:ethyl acetate as eluant, collecting 100 ml fractions. Evaporation of fractions 14 and 15 gave purified title product as an oil, 2.03 g (39% over-all); [alpha]$_D$=−104.57° (c=0.53 in CHCl$_3$).

EXAMPLE 17

3S-Bromothiolane 1-S-Oxide (IXb)

By the method of Example 3, 29.3 g (0.175 mol) (S)-3-bromothiolane was converted to present title product as a white solid (88%). If desired, the product (10.1 g) was further purified by flash chromatography on a 90 mm×15 cm silica gel column eluting with ethyl acetate in 100 ml fractions. Fractions 36–64 were stripped to yield 4.73 g of purified title product; m.p. 68°–70° C.; [alpha]$_D$=−99.94° (c=5 in CHCl$_3$).

Analysis calculated for C$_4$H$_7$OBrS: C, 26.64; H, 3.86; S, 17.52%; Found: C, 26.47; H, 3.89; S, 17.71%.

EXAMPLE 18

3R-(Acetylthio)thiolane 1S-Oxide

By the method of Example 4, the product of the preceding Example (24 g) was converted to crude title product which crystallized on pumping under high vacuum, 26 g. The latter was purified by flash chromatography on a 500 mm×24 cm silica gel column using 49:1 ethyl acetate:methanol as eluant collecting 125 ml fractions. Fractions 50–90 were combined and stripped to yield purified title product, 19.6 g (85%); m.p. 54°–56° C.; [alpha]$_D$=+85.73° (c=1 in CHCl$_3$). A sample was recrystallized from isopropyl ether; m.p. 57°–59° C.

Analysis calculated for C$_6$H$_{10}$O$_2$S$_2$: C, 40.42; H, 5.65%. Found: C, 40.69; H, 5.45%.

EXAMPLE 19

3S,4R-3-[1R-(Dimethyl-t-butylsilyloxy)-ethyl]-4-1S-oxo-3R-thiolanylthio(thiocarbonylthio)-2-azetidinone (V, R$^7$=H, R$^6$=Me$_2$tBuSi)

Sodium metal (2.23 g, 0.097 mol) was suspended in 340 ml dry isopropyl alcohol and refluxed 2.5 hours to produce a clear solution of sodium isopropoxide, then cooled to room temperature. Meanwhile, under nitrogen in a flame-dried flask, the product of the preceding Example (18.1 g, 0.102 mol) was dissolved in 260 ml dry isopropyl alcohol and cooled to 0° C. With stirring the sodium isopropoxide solution was added over 17 minutes; maintaining 0°-2° C. After stirring for an additional 30 minutes at 0° C., the mixture was chilled to −30° C. and carbon disulfide (23.3 g, 18.4 ml, 0.306 mol) in 50 ml isopropyl alcohol added dropwise. The resulting yellow suspension was warmed to 0° C. and stirred an additional 10 minutes, thus producing sodium 3R-(thio(thiocarbonyl)thio)thiolane 1S-oxide.

To the latter suspension was added dropwise a solution of 3R,4R-4-acetoxy-3-[1R-(dimethyl-t -butylsilyloxy)ethyl]-2-azetidinone (32.1 g, 0.112 mol), maintaining 0°-3° C. After stirring at 0°-2° C. an additional 20 minutes, the reaction mixture was poured into 900 ml saturated NH$_4$Cl and 900 ml ethyl acetate, and diluted with an additional 2,250 ml of ethyl acetate. The organic layer was separated, washed sequentially with 1 ×900 ml H$_2$O, 1×900 ml 20% CaCl$_2$, 1×900 ml H$_2$O, 1×900 ml 20% CaCl$_2$ and 2×900 ml saturated NaCl, dried (Na$_2$SO$_4$), filtered and stripped in vacuo to solids, which were dried by repeated addition of 1:1 ethyl acetate:hexane and stripping. The solid residue was repulped in 300 ml hexane and title product recovered by filtration, 37.0 g. The latter was twice recrystallized by dissolving in 50-60 ml of acetone, with crystallization induced by the slow addition, with stirring, of 500 ml of isopropyl ether to yield purified title product, 26.4 g; m.p. 90°-94° (dec.); [alpha]$_{D}$= +315.05° (c=1 in CHCl$_3$); ir(KBr) 1766 cm$^{-1}$.

EXAMPLE 20

3S,4R-N-[(2-Chloroallyloxy)oxalyl]-3-[1R-(dimethyl-t-butylsilyloxy)ethyl]-4-[1S-oxo-3R-thiolanylthio(thiocarbonyl)thio]-2-azetidinone (V, R$^6$=Me$_2$tBuSi, R$^7$=COCOCH$_2$CClCH$_2$)

A flame-dried, three-neck flask equipped with a dropping funnel and low temperature thermometer under a N$_2$ atmosphere was charged with the product of the preceding Example (26.4 g, 60 mmol) and 300 ml dry methylene chloride (passed through neutral alumina). The reaction was cooled to −60° C. internal temperature and N,N-diisopropylethylamine (13.6 ml, 78 mmol) was added via syringe followed by 2-chloroallyl oxalofluoride (13.0 g, 78 mmol), which was added dropwise maintaining −60° to −55° C. The reaction was then stirred at −50° to −55° C. for 50 minutes, quenched with 100 ml H$_2$O, warmed to 0° C. and diluted with an additional 100 ml H$_2$O. The organic layer was separated, washed with an additional 2×200 ml H$_2$O, 2×200 ml pH 7 buffer and 200 ml brine, dried over Na$_2$SO$_4$, filtered and concentrated in vacuo to yield title product, 33.2 g of a yellow foam, which was used directly in the next step.

EXAMPLE 21

2-Chloroallyl 5R,6S-6-[1R-(Dimethyl-t -butylsilyloxy)ethyl]-2-(1S-oxo-3R-thiolanylthio)-2-penem-3-carboxylate (III, R$^4$=Me$_2$tBuSi, R$^5$=CH$_2$CClCH$_2$)

By the method of Example 8, the entire batch of crude product from the preceding Example (33.2 g, 0.060 mol assumed) was converted to present title product, crystallized from ethyl acetate/diisopropyl ether in like manner to yield 11.3 g. The latter was further purified by repulping in 200 ml diisopropyl ether to yield 9.8 g; m.p. 122°-125° C. (dec.); ir(KBr) 1,784 cm$^{-1}$; [alpha]$_{D}$= +158.13° (c=1 in CHCl$_3$).

EXAMPLE 22

2-Chloroallyl 5R,6S-6-(1R-Hydroxyethyl)-2-(1S-oxo-3R-thiolanylthio)-2-penem-3-carboxylate (III, R$^4$=H, R$^5$=CH$_2$CClCH$_2$)

By the method of Example 9, the product of the preceding Example (6.0 g, 11.2 mmol) was converted to crude title product. The latter was slurried in 60 ml of ethyl acetate to produce purified title product as a white solid, 4.0 g; m.p. 156°-158° C. (dec.); [alpha]$_{D}$= +186.7° (c=0.35 in dimethylsulfoxide).

EXAMPLE 23

5R,6S-6-(1R-Hydroxyethyl)-2-(1R-oxo-3S -thiolanylthio)-2-penem-3-carboxylic Acid (I, R =H)

By the method of Example 10, the product of the preceding Example (4.24 g, 10 mmol) was converted to crude sodium salt of title product (4.56 g), which was slurried in 50 ml of ethyl acetate for 1 hour to yield partially purified sodium salt, 4.36 g. The latter was converted to freeze-dried sodium salt according to Example 10. The entire batch of freeze-dried sodium salt was redissolved in 11 ml H$_2$O, cooled to 0°-5° C. and the pH slowly lowered from 6.9 to 4.0 with 3N HCl. Crystallization was induced by scratching, and the pH was then slowly lowered to 2.5. Title product was recovered by filtration, with repulp in 20 ml of hplc grade ethyl acetate, 2.6 g; m.p. 185°-187° C. (dec.); [alpha]$_{D}$= +128.67 (c=1 in dimethylsulfoxide).

Sterile sodium salt was prepared according to Example 12 (2.3 g from 2.2 g of acid); m.p. 120°-123° C. (gassing); [alpha]$_{D}$= +115.29 (c=2.1 in H$_2$O).

EXAMPLE 24

Tetrabutylammonium 5R,6S-6-[1R-(dimethyl -t-butylsilyloxy)ethyl]-2-(1R-oxo-3S -thiolanylthio)-2-penem-3-carboxylate (III, R$^4$=Me$_2$tBuSi, R$^5$=TBA Salt)

By the method of Example 10, the product of Example 21 (1.2 g, 2.23 mol) was converted to sodium 5R,6S-6-[1R-(dimethyl-t-butylsilyl)ethyl]-2-(1R-oxo-3S -thiolanylthio)-2-penem-3-carboxylate in CH$_2$Cl$_2$. The reaction mixture was diluted with 50 ml ethyl acetate, 10 ml ether and 50 ml hexane, then extracted 5×25 ml of H$_2$O to yield an aqueous solution of the sodium salt. To the combined aqueous extracts was added a solution of tetrabutylammonium hydrogen sulfate (0.76 g, 2.23 mmol) and NaHCO$_3$ (0.375 g, 4.46 mmol) in 10 ml H$_2$O. The solution was stirred 20 minutes, then extracted 3×140 ml CH$_2$Cl$_2$, and the extracts combined, dried (Na$_2$SO$_4$), carbon treated, filtered and stripped to yield title product as a foam, 1.29 g; pnmr(CDCl$_3$)delta(ppm) 300 MHz: 0.06 (s, 6H), 0.85 (s, 9H), 0.78 (t, 12H), 1.25 (d, 3H), 1.28-1.50 (m, 8H), 1.50-1.70 (m, 8H), 2.40-2.80 (m, 4H), 2.90-3.10 (m, 1H), 3.22-3.38 (t, 8H), 3.45-3.55 (m, 2H), 3.90-4.02 (m, 1H), 4.05-4.20 (m, 1H), 5.42 (s, 1H).

EXAMPLE 25

Pivaloyloxymethyl 5R,6S-6-[1R-(Dimethyl-t -butylsilyloxy)ethyl]-2-(1R-oxo-3S-thiolanylthio) -2-penem-3-carboxylate (III, R$^4$=Me$_2$tBuSi, R$^5$=CH$_2$—O—CO—C(CH$_3$)$_3$)

By the method of Example 14, the product of the preceding Example (1.29 g, 1.8 mmol) was converted to title product, initially isolated as a brownish oil which was flash chromatographed on a 50 mm×25 cm silica gel column eluting with 19:1 ethyl acetate in 50 ml fractions. Fractions 14–20 were combined and stripped to yield title product as a solid, 0.64 g; pnmr(CDCl$_3$)delta(ppm) 300 MHz: 0.08 (s, 6H), 0.88 (s, 9H), 6.22 (s, 9H), 1.25 (d, 3H), 2.6–2.85 (m, 4H), 3.08–3.20 (m, 1H), 3.60–3.78 (m, 2H), 3.90–4.00 (m, 1H), 4.2–4.3 (m, 1H), 5.65 (s, 1H), 5.86 (q, 2H, $J_{AB}$=12.5 Hz).

EXAMPLE 26

Pivaloyloxymethyl 5R,6S-6-(1R-hydroxy-ethyl)-2-(1R-oxo-3S-thiolanylthio)-2-penem-3-carboxylate (I, R=CH$_2$—O—CO—C(CH$_3$)$_3$)

By the method of Example 9, the product of the preceding Example (0.638 g, 1.104 mmol) was converted to crude title product which was chromatographed on a 50 mm×25 cm silica gel column collecting 50 ml fractions; 1:9 ethyl acetate:tetrahydrofuran was the eluant for fractions 1–12, pure tetrahydrofuran for fractions 13–20. The latter fractions were combined, stripped and the solid residue (422 mg) repulped in 15 ml of 2:1 petroleum ether:ethyl acetate and then 22 ml of 10:1 petroleum ether:ethyl acetate to yield purified title product, 0.314 g; m.p. 162°–164° C. (dec.); [alpha]$_D$= +109.7° (c=0.5 in dimethylsulfoxide); pnmr(CDCl$_3$)delta(ppm) 250 MHz: 1.20 (s, 9H), 1.34 (d, 3H, J =6.3 Hz), 2.12 (d, 1H), 2.6–2.9 (m, 4H), 3.06–3.22 (m, 1H), 3.60–3.75 (m, 2H), 3.85–3.98 (m, 1H), 4.2–4.35 (m, 1H), 5.68 (s, 1H), 5.86 (q, 2H, $J_{AB}$=12.5 Hz).

EXAMPLE 27

Allyl 5R,6S-6-(1R-Hydroxyethyl)-2-1R-oxo-3S-thiolanylthio) -2-penem-3-carboxylate (IV, R$^4$=H, R$^5$=CH$_2$CHCH$_2$ Using the methods of Examples 7–9, substituting equivalent allyl oxalofluoride in place of 2-chloroallyl oxalofluoride in Example 7, the product of Example 6 is converted to present title product.

PREPARATION 1

[(2-Chloroallyl Oxalofluoride [(2-Chloroallyloxy)oxalyl Fluoride] CH$_2$=CClCH$_2$O(CO)COF Under dry N$_2$ in flame dried glass apparatus, cesium fluoride (167 g, 1.1 mol) was placed in a 1 liter single neck flask and placed under high vacuum and gently heated with a flame until the solid became free flowing, then cooled to room temperature. Acetonitrile, distilled from CaH$_2$ (183 ml) was added and the mixture cooled to −20° C. internal temperature. 2-Chloroallyl oxalochloride (183 g, 1.0 mol) was added dropwise over a 30 minute period and the mixture slowly warmed to room temperature, stirred at that temperature for 16 hours, and byproduct cesium chloride recovered by filtration with acetonitrile wash. The filtrate and wash were combined and stripped, and the residue distilled at reduced temperature to yield 129 g (77%) of the desired product, b.p. 62°–64° C./22 mm.

IR(CHCl$_3$) cm$^{-1}$ 1,770, 1,870.

$^1$H-NMR(CDCl$_3$)delta(ppm) 4.80 (s, 2H), 5.4–5.6 (m, 2H).

PREPARATION 2

Allyl Oxalofluoride [Allyloxalyl Fluoride] CH$_2$=CHCH$_2$O(CO)COF

By the procedure of the preceding Preparation, allyl oxalochloride (252.5 g, 1.70 mol) and cesium fluoride (284 g, 1.87 mol) were converted to twice distilled title product, b.p. 48°–50° C./35 mm; 124°–126° C. (atmospheric pressure).

$^1$H-NMR(CDCl$_3$)250 MH$_3$, delta: 4.76 (d, 2H, J=6 Hz), 5.28 (dd, 1H, J=1, 7 Hz), 5.37 (dd, 1H, J=1, 17 Hz), 5.90 (ddt, 1H, J=6, 11, 17 Hz).

$^{13}$C-NMR(CDCl$_3$)63 MHz, delta: 68.5 (t), 120.4 (t), 129.7 (d), 146.3 (d, $J_{C-F}$=375 Hz), 153.0 (d, $J_{C-C-F}$=87 Hz). IR(neat) 1,860 (C=O), 1,770 (C=O), 1,120 cm$^{-1}$.

PREPARATION 3

2-Chloroallyl Oxalochloride [(2-Chloroallyloxy)oxalyl Chloride]

Oxalyl chloride (130 ml, 1.49 mol) was placed in a dry 3-neck flask under N$_2$ and cooled to 0° C. With stirring, 2-chloroallyl alcohol (138 g, 1.49 mol) was added dropwise in a manner which maintained the temperature at 0°–2° C. and controlled the vigorous evolution of HCl, then allowed to warm to room temperature and held 16 hours and distilled to yield title product, 214 g, b.p. 82°–84° C./23 mm.

PREPARATION 4

Benzyl Oxalochloride [(Benzyloxy)oxalyl Chloride]

Under N$_2$, oxalyl chloride (262 ml) was dissolved in 1 liter anhydrous ether and heated to reflux, at which temperature benzyl alcohol (207 ml) was added over 70 minutes. After refluxing a further 16 hours, ether was stripped and the residue distilled at reduced pressure to yield 372 g (94%) of title product, b.p./0.7 mm 85° C.

PREPARATION 5

Oxalic Acid, Half Benzyl Ester

Title product of the preceding Preparation (180 g, 0.91 mol) in 800 ml ether was cooled in an acetone-dry ice bath. As the mixture was allowed to warm to 0° C., aqueous NH$_4$OH (2M, 906 ml, 0.91 mol) was added portion-wise. The mixture was then warmed to room temperature, stirred 1 hour, and the pH adjusted to 8.5 with 95 ml 2M NH$_4$OH. The aqueous layer was separated, extracted 2×400 ml ether, layered with 500 ml fresh ether, cooled to 10° C. and the pH adjusted to 1.5 with 2M HCl. The layers were separated, the aqueous layer extracted 2×400 ml ether, and the three acidic organic layers combined, washed with 500 ml brine, dried over Na$_2$SO$_4$ and stripped to yield title product as white solids, 163 g. $^1$H-NMR(CDCl$_3$)delta(ppm): 5.2 (s, 1H), 6.95 (s, 2H), 7.3 (s, 5H).

PREPARATION 6

Benzyl Pivaloyloxymethyl Oxalate

The product of the preceding Preparation (163 g, 0.91 mol) was dissolved in 1 liter CHCl$_3$ and carefully neutralized (foaming) with NaHCO$_3$ (76.2 g, 0.91 mol). Separately, tetrabutylammonium hydrogen sulfate (308 g, 0.91 mol) in 1.5 liters H$_2$O was carefully neutralized with a like quantity of NaHCO$_3$. The former slurry was added slowly to the latter solution, the mixture stirred vigorously for 20 minutes, the aqueous layer separated and washed with 500 ml fresh CHCl$_3$. The organic layers were combined, dried over Na$_2$SO$_4$ and stripped to yield tetrabutylammonium benzyl oxalate, 478 g. The latter was taken up in 400 ml acetone. Chloromethyl pivalate (118 ml, 0.82 mol) was added and the mixture stirred under N$_2$ for 16 hours at ambient temperature.

The acetone was stripped, and the residue taken up in 1 liter ethyl acetate, washed 4×500 ml H₂O and 1×500 ml brine, dried over Na₂SO₄ and stripped to yield title product as an oil, 201 g; tlc Rf 0.60 (2:3 ethyl acetate:-hexane).

¹H-NMR(CDCl₃, 90 MHz)delta(ppm): 1.21 (s, 9H), 5.2 (s, 2H), 5.8 (s, 2H), 7.3 (s, 5H).

PREPARATION 7

Oxalic Acid, Half Pivaloyloxymethyl Ester

Title product of the preceding Preparation (27.3 g, 0.093 mol) and 2.8 g of 10% Pd/C were combined in 150 ml ethyl acetate and hydrogenated in a Paar hydrogenation apparatus at 4× atmospheric pressure and ambient temperature for 1.5 hours. The catalyst was recovered by filtration over diatomaceous earth and the filtrate stripped to yield title product as an oil, 19.3 g.

¹H-NMR(CDCl₃, 90 MHz)delta(ppm): 1.21 (s, 9H), 5.96 (s, 2H), 10.31 (s, 1H).

PREPARATION 8

Pivaloyloxymethyl Oxalochloride

Title product of the preceding Preparation (19.2 g, 0.094 mol) was dissolved in 20 ml benzene and added portionwise over 20 minutes to oxalyl chloride (47.7 g, 33 ml, 0.376 mol) in 100 ml benzene. After 30 minutes, the mixture was stripped and the residue (19.2 g) distilled to yield title product, 16.4 g; b.p. 83° C./0.4 mm.

PREPARATION 9

Pivaloyloxymethyl Oxalofluoride
Pivaloyloxymethyloxalyl Fluoride]
(CH₃)₃C(CO)OCH₂O(CO)COF Potassium fluorosulfinate (80% KSO₂F, 2.40 g, 1.92 g corrected, 0.016 mol) was added to oxalyl chloride (3.50 g, 0.016 mol) and the mixture gradually warmed in an oil bath to 60° C., at which point vigorous gas evolution began. The bath was removed. Once the reaction subsided, the oil bath was replaced, the mixture warmed to 80° C. and held for 15 minutes, cooled to 60° C. and distilled from a bath at 60° C. to yield title product, 1.19 g; b.p. 52°-54° C./0.4 mm.; solidified on storage at −50° C., melts at ambient temperature.

¹³C-NMR: 176.6, 152.6 and 151.5, 148.1 and 140.2, 81.7, 38.8, and 26.6, with splitting of oxalate carbonyls 89 Hz and 252.6 Hz.

PREPARATION 10

(S)-2-Bromosuccinic Acid

To a solution of 1,000 g (9.72 mol) sodium bromide in 2.1 liters 6N sulfuric acid under nitrogen was added 323.1 g (2.43 mol) L-aspartic acid and the resulting solution cooled to 5° C. To this was added in portions over 1.5 hours, 201.4 g (2.92 mol) sodium nitrite while keeping the temperature below 10° C. After the addition was completed, one liter of distilled water was added, followed by 73.07 g (1.22 mol) urea. The resulting mixture was poured into a separatory funnel and extracted with 2.5 liters ethyl ether. To the aqueous layer was added 500 g sodium chloride, and the mixture extracted three times with ether (3×1.25 liters). The combined ether layers were washed with brine, dried (Na₂SO₄) and the solvent evaporated in vacuo to yield 303 g (63%) of the desired compound; [alpha]$_D$= −73.5° (c=0.6 in ethyl acetate); m.p. 185° C.

PREPARATION 11

(S)-2-Bromo-1,4-butanediol

Employing flame-dried glassware under nitrogen, 303.14 g (1.54 mol) (S)-2-bromosuccinic acid was dissolved in 3.2 liters anhydrous tetrahydrofuran (THF) and the mixture cooled to −20° C. To this was added dropwise over 90 minutes, a solution of 350.78 g borane-methyl sulfide complex in 438 ml of tetrahydrofuran (4.62 mol). The mixture was stirred while warming slowly to 18° C. whereupon the reaction mixture liberated hydrogen gas and became exothermic. The mixture was cooled in dry ice/acetone while passing nitrogen over the mixture. After 15 minutes the cooling bath was removed, and the reaction allowed to warm to ambient temperature and maintained under a sweep of nitrogen for 60 hours. A liter of methanol was added slowly, the sweep of nitrogen continued for 30 minutes, and the solvents then evaporated. The residue was taken up in one liter methanol and solvent evaporated again. This was repeated two more times to obtain 282.41 g (100%) of the desired diol.

PREPARATION 12

(R)-(2-Methanesulfonyloxyethyl)oxirane

A. Employing dry glassware, under nitrogen, 20 g (0.118 mol) (S)-2-bromo-1,4-butanediol was dissolved in 400 ml dry methylene chloride and 69.41 g (0.213 mol) cesium carbonate was added. The mixture was stirred at room temperature for 40 hours and then filtered with CH₂Cl₂ wash. The combined filtrate and wash liquor was used directly in Part B below. When desired, the solvent was stripped to yield intermediate (R)-(2-hydroxyethyl)oxirane in virtually quantitative yield. B. In a flame-dried flask, under nitrogen, was added the entire product solution from Part A (about 800 ml), which was then cooled to −25° C. Triethylamine (21.55 g, 0.213 mol) was added followed by slow addition of 20.34 g (0.178 mol) of methanesulfonyl chloride over 25 minutes, maintaining less than −20° C. The resulting mixture was allowed to warm to room temperature over 1.5 hours, extracted 1×50 ml pH 4 buffer, and the buffer back-extracted 3×50 ml CH₂Cl₂. The organic extracts were combined with the original organic layer, extracted 1×50 ml saturated NaCl, and the brine back-extracted with 3×50 ml CH₂Cl₂ and the organic extracts combined with the original organic layer, which was stripped to yield title product in substantially quantitative yield; [alpha]$_D$=+34.7° (c=0.1 in CH₂Cl₂); pnmr(CDCl₃)delta(ppm): 1.76–1.85 (1H, m, CH), 2.02–2.11 (1H, m, CH), 2.50–2.52 (1H, m, CHO), 2.77–2.80 (1H, m, CHO), 2.98–3.04 (1H, m, CHO), 2.99 (3H, s, CH₃), 4.32 (2H, t, CH₂O).

PREPARATION 13

(S)-2-Bromo-1,4-di(methanesulfonyloxy)butane

A solution of 70 g (0.414 mol) (S)-2-bromo -1,4-butanediol in 1.5 liters methylene chloride was cooled in ice and 173 ml (1.24 mol) triethylamine (dried over potassium hydroxide) was added to give a clear solution. To this was added dropwise over 80 minutes at 5° to 15° C., 96 ml (1.24 mol) methanesulfonyl chloride. The mixture was then stirred at room temperature for 2.5 hours, washed 2×750 ml with water and 1×750 ml brine, dried (MgSO₄), and the solvent evaporated to give an amber oil which was purified by chromatography on a 140 mm×25 cm silica gel column, eluting with 9:1 chloroform:ethyl acetate. The product fractions were combined and solvent evaporated to give 105 g (97%) of the title compound as a waxy white solid; [alpha]$_D$= −34.49° (c=5 in CHCl$_3$).

I claim:

1. A compound having the absolute stereochemical formula

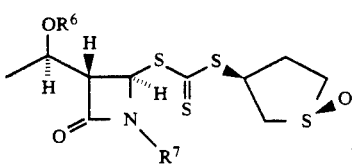

(VI)

wherein R$^6$ is a conventional silyl protecting group; R$^7$ is hydrogen or

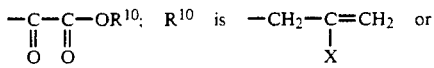

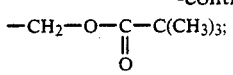

and

X is hydrogen or chloro.

2. The compound of claim 1 wherein R$^6$ is dimethyl(t-butyl)silyl and R$^7$ is hydrogen.

3. A compound of claim 1 wherein R$^6$ is dimethyl(t-butyl)silyl and R$^7$ is

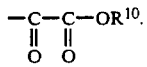

4. The compound of claim 3 wherein R$^{10}$ is

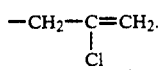

5. The compound of claim 3 wherein R$^{10}$ is

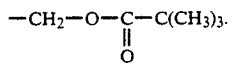

* * * * *